(12) United States Patent  
Yamakawa et al.

(10) Patent No.: US 11,106,178 B2  
(45) Date of Patent: Aug. 31, 2021

(54) CELL OBSERVATION DEVICE

(71) Applicant: SHIMADZU CORPORATION, Kyoto (JP)

(72) Inventors: Momoyo Yamakawa, Kyoto (JP); Shuhei Yamamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 205 days.

(21) Appl. No.: 16/490,131

(22) PCT Filed: Mar. 3, 2017

(86) PCT No.: PCT/JP2017/008568  
§ 371 (c)(1),  
(2) Date: Oct. 22, 2019

(87) PCT Pub. No.: WO2018/158947  
PCT Pub. Date: Sep. 7, 2018

(65) Prior Publication Data  
US 2020/0096940 A1   Mar. 26, 2020

(51) Int. Cl.  
*G03H 1/00* (2006.01)  
*G01N 21/45* (2006.01)  
(Continued)

(52) U.S. Cl.  
CPC ......... *G03H 1/0005* (2013.01); *G01N 21/453* (2013.01); *G03H 1/0443* (2013.01);  
(Continued)

(58) Field of Classification Search  
None  
See application file for complete search history.

(56) References Cited

U.S. PATENT DOCUMENTS

2007/0159688 A1* 7/2007 Descour ............... G02B 21/34  
359/368  
2008/0137933 A1   6/2008 Kim  
(Continued)

FOREIGN PATENT DOCUMENTS

CN   102712890 A   10/2012  
JP   10-268740 A   10/1998  
(Continued)

OTHER PUBLICATIONS

Peng Bao et al., "Lensless phase microscopy using phase retrieval with multiple illumination wavelengths," Applied Optics, Aug. 1, 2012, pp. 5486-5494, vol. 51, No. 22.  
(Continued)

*Primary Examiner* — Jennifer D. Carruth  
(74) *Attorney, Agent, or Firm* — Sughrue Mion, PLLC (57) ABSTRACT

In a microscopic observation unit (10), hologram data is acquired at each measurement position on a cell culture plate (13) while a light-source section (11) and other related sections are gradually moved by a moving section (15). Every time a set of data for one measurement position is acquired, a measurement monitoring image creator (24) creates a thumbnail image by reducing the size of a hologram image which is based on original data (two-dimensional distribution of light intensity). A display processor (25) pastes the create thumbnail image to progressively complete the hologram image of the entire plate to be displayed on a display unit (27). A measurement operator watches the hologram image during the execution of the measurement. When it has been concluded that the ongoing measurement is inappropriate, the operator presses a measurement stop button to immediately discontinue the measurement. Thus, When there is a problem with the measurement, such as a foreign object mixed in the sample, the measurement can be discontinued before a phase image or (Continued)

intensity image based on the hologram data is reconstructed on the server after the completion of the entire measurement, so as to avoid wasting time for the useless measurement.

6 Claims, 5 Drawing Sheets

(51) Int. Cl.
  *G03H 1/04* (2006.01)
  *G03H 1/22* (2006.01)
(52) U.S. Cl.
  CPC ......... *G03H 1/22* (2013.01); *G03H 2001/005* (2013.01); *G03H 2001/0452* (2013.01)

(56) References Cited

U.S. PATENT DOCUMENTS

| | | |
|---|---|---|
| 2013/0027539 A1 | 1/2013 | Kiyota et al. |
| 2014/0300696 A1 | 10/2014 | Ozcan et al. |
| 2016/0252880 A1* | 9/2016 | S Nchez Ortiga . G02B 13/0095 359/30 |
| 2017/0219999 A1* | 8/2017 | Serabyn ............... G03H 1/0443 |
| 2017/0329281 A1 | 11/2017 | Tagawa |
| 2019/0072897 A1* | 3/2019 | Jepsen ................. G03H 1/0465 |
| 2020/0096940 A1* | 3/2020 | Yamakawa .......... G03H 1/0005 |
| 2020/0271949 A1* | 8/2020 | Colin .................... G02B 30/40 |

FOREIGN PATENT DOCUMENTS

| | | |
|---|---|---|
| JP | 2004-012201 A | 1/2004 |
| JP | 2009-175330 A | 8/2009 |
| JP | 2011-170212 A | 9/2011 |
| WO | 2007/002898 A2 | 1/2007 |
| WO | 2011/089908 A1 | 7/2011 |
| WO | 2013/070287 A1 | 5/2013 |
| WO | 2016/084420 A1 | 6/2016 |

OTHER PUBLICATIONS

Written Opinion of the International Searching Authority of PCT/JP2017/008568 dated May 23, 2017.
International Search Report of PCT/JP2017/008568 dated May 23, 2017.

* cited by examiner

Fig. 8

CELL OBSERVATION DEVICE

CROSS REFERENCE TO RELATED APPLICATIONS

This application is a National Stage of International Application No. PCT/JP2017/008568 filed Mar. 3, 2017.

TECHNICAL FIELD

The present invention relates to a cell observation device for observing the state of a cell, and more specifically, to a cell observation device configured to obtain a hologram which records an interference pattern formed by object wave and reference wave by means of a holographic microscope, and to create a phase image, intensity image or other types of images after computing phase information or intensity information based on the hologram data.

BACKGROUND ART

In recent years, studies which use pluripotent stem cells, such as induced pluripotent stem cells (iPS cells) or embryonic stem cells (ES cells), have been popularly conducted in the area of regenerative medicine. In general, cells are transparent and difficult to observe with a normal optical microscope. Accordingly, phase-contrast microscopes have been commonly used for the observation of the cells. A problem with the phase-contrast microscope is that it requires the focusing operation before recording the microscopic image, so that a significant amount of time is required for the measurement when it is necessary to take a microscopic image for each of the small areas defined by dividing a large observation target area. In order to solve such a problem, in recent years, a digital holographic microscope which employs the technique of digital holography has been developed and put to practical use (for example, see Patent Literature 1 or 2).

A digital holographic microscope obtains an interference pattern (hologram) formed on the detection plane of an image sensor or similar device by object light, which is a beam of light reflected by or transmitted through an object illuminated with a beam of light from a light source, and reference light, which is a beam of light from the same light source and reaches the detection surface without interacting with the object. A backpropagation calculation of light waves or similar computational processing based on the hologram is performed to acquire phase information or amplitude (intensity) information as well as create an intensity image or phase image as a reconstructed image. Such a digital holographic microscope allows for the retrieval of phase information and other kinds of information at a desired distance in the stage of the computational processing after the acquisition of the hologram. Therefore, it is unnecessary to perform the focusing for every shot of image.

Digital holographic microscopes can be divided into several types, such as an in-line type, off-axis type and phase-shift type. A major difference between these types exists in the configuration of the optical system used for obtaining a hologram. In the case of the off-axis type, a beam of light generated from a laser light source is normally divided into a reference beam and an illumination beam which illuminates an object. An object beam transmitted through the object illuminated with the illumination beam is made to be incident on an image sensor at one incident angle, while the reference beam is made to be incident on the same image sensor at a different incident angle. In the case of the in-line type, a beam of light generated from a laser light source is cast onto an object without being split into two beams. The object beam transmitted through the object, and the reference beam which is transmitted through an area in the vicinity of the object without passing through the object, are both made to be incident on an image sensor at substantially right angles. In the case of the phase-shift type, the optical path length of the reference beam produced by a beam splitter is varied in multiple steps in a phase-shift interferometer to obtain a hologram with different multiple phases.

Any of those types of digital holographic microscopes requires a computer for computing the phase and amplitude information of the light waves based on the acquired hologram data and for visualizing the computed information. For example, Patent Literature 1, Non-Patent Literature 1 or other related documents propose phase-retrieving methods which include repetitive calculations of light-wave propagation based on holograms related to multiple wavelengths of light acquired with an in-line digital holographic microscope. Such a computation is considerably complex and requires a significant amount of calculation.

A cell observation device for observing biological cells being cultured must be capable of creating images with a sufficiently high level of resolution that enables detailed observation of individual cells over a large area which includes the entire cell culture plate or all wells formed on the plate. In order to obtain such a phase image or intensity image with a cell observation device which employs a digital holographic microscope, it is necessary to divide the observation target area (e.g. the entire cell culture plate) into a considerable number of small areas and acquire a hologram for each of those small areas. Furthermore, a computational process based on the hologram must be performed to determine the two-dimensional distribution of the phase information or amplitude information for each small area. The two-dimensional distributions obtained in this manner for the large number of small areas must be eventually combined together to reconstruct an image for the observation target area.

As noted earlier, in the first place, the amount of computation for calculating the phase information or other necessary kinds of information and reconstructing an image is considerably large. Performing such a computation for a large number of small areas means that the amount of computation will be enormous. Therefore, even a computer with a high level of power requires a certain length of time from the beginning of the measurement to the completion of the reproduction of the phase image for the observation target area.

For example, according to a study by the present inventors, a device which is configured to divide the entire cell culture plate into approximately 800 small areas and acquire holograms related to multiple wavelengths and with a high level of resolution (e.g. 4000×3000 pixels per image) for each small area will require one hour or an even longer period of time from the beginning of the measurement to the completion of the reconstruction of the phase image. In other words, it is not until a one-hour or longer period passes from the beginning of the measurement that the phase image or intensity image of the sample to be observed is available for observation.

A measurement will be completely useless if there is a problem with the cell culture plate being observed, such as the presence of a foreign object in the plate, or if the measurement is unsuccessful or improperly conducted. As just explained, such a problem will not be revealed until a considerable amount of time passes from the beginning of the measurement. This means that the measurement results in a waste of time and lowers the efficiency of the tasks of observing and analyzing the cells.

CITATION LIST

Patent Literature

Patent Literature 1: WO 2016/084420 A
Patent Literature 2: JP 10-268740 A

Non-Patent Literature

Non Patent Literature 1: Peng Bao and three other authors, "Lensless phase microscopy using phase retrieval with multiple illumination wavelengths", *Applied Optics*, The Optical Society of America, 2012, Vol. 51, No. 22, pp. 5486-5494

SUMMARY OF INVENTION

Technical Problem

The present invention has been developed to solve the previously described problem. In a cell observation device configured to reconstruct a phase image or intensity image of a sample containing cells by performing the phase retrieval or similar computational processing based on a hologram obtained with a digital holographic microscope, the object of the present invention is to provide a cell observation device which allows users to promptly recognize an occurrence of a problem with the sample or improper handling in the measurement, and to avoid the acquisition of unwanted data.

Solution to Problem

The present invention developed for solving the previously described problem is a cell observation device employing a digital holographic microscope, including:
  a) a light-source section configured to generate coherent output light;
  b) a detector section configured to obtain a hologram which is an interference pattern formed by reference wave and object wave when a sample containing a cell is illuminated with the output light of the light-source section;
  c) a moving section configured to move either the light-source section and the detector section or the sample, or both, so as to change a measurement position on the sample;
  d) a measurement controller configured to control the light-source section, the detector section and the moving section so as to repeatedly change the measurement position from one position to another on the sample by the moving section and acquire a hologram at each measurement position within a predetermined observation target area;
  e) a reconstructed image creator configured to compute phase information based on hologram data acquired with the detector section under the control of the measurement controller, and to create an image showing a two-dimensional distribution of the phase information;
  f) a measurement monitoring image creator configured to create a hologram image showing a light-intensity distribution within a portion or the entirety of the observation target area during an execution of a measurement under the control of the measurement controller based on the hologram data acquired with the detector section on measurement positions for which the measurement is already completed; and
  g) a display processor configured to display, on a display section, the hologram image created by the measurement monitoring image creator.

In the cell observation microscope according to the present invention, a typical example of the sample is a cell culture container, in which case the largest possible area for which hologram data can be obtained with the holographic microscope may be the entire cell culture container or a partial area of the container. Examples of the cell culture container include a cell culture plate with one or more wells formed on its surface, a petri dish, and a culture flask designed for mass culture. Accordingly, the cell observation device according to the present invention is a device that is suitable for observing biological cells being cultured in the aforementioned kinds of cell culture containers.

In the cell observation device according to the present invention, the moving section may be configured, for example, to move the light-source section and the detector section as an integral structure with respect to a statically placed cell culture plate so as to change the measurement position at which the coherent light from the light-source section is incident on the cell culture plate. The measurement controller may operate the moving section to move, for example, the light-source section and the detector section in a stepwise manner while repeating the operation of illuminating one measurement position within the cell culture plate with the coherent light and acquiring hologram data, i.e. a set of data which shows a two-dimensional distribution of the light intensity due to the hologram formed by the light on the detection surface of the detector section.

The reconstructed image creator performs a computation for obtaining phase information based on the hologram data acquired with the detector section. Meanwhile, the measurement monitoring image creator produces a hologram image which shows the light intensity distribution within a portion or the entirety of the observation target area during the execution of the measurement, based on the hologram data acquired for the measurement positions for which the measurement is already completed. Every time a set of hologram data related to one measurement position is newly acquired with the progress of the measurement, the measurement monitoring image creator updates the hologram image which shows the light intensity distribution within a portion or the entirety of the observation target area. In other words, this hologram image is updated almost in real time with the progress of the measurement.

The hologram image created by the measurement monitoring image creator shows a two-dimensional distribution of the light intensity corresponding to a hologram. On this type of image, biological cells cannot be sufficiently visible since they are transparent and low in profile, whereas the same image gives a sufficiently clear and recognizable view for larger structures, such as a foreign object having a certain size or the edge of a well having a considerable difference in height. By viewing this hologram image displayed on the display section during the execution of the measurement, the user (measurement operator) can check for the presence of a foreign object other than the biological cells as well as the appropriateness of the measurement. If the user considers that it is unnecessary to continue the measurement, the user can stop the measurement halfway to avoid the execution of the useless measurement.

The digital holographic microscope in the cell observation device according to the present invention may be any type of system, such as an in-line type, off-axis type or phase-shift type, although an in-line type of configuration which uses holograms at a plurality of wavelengths is preferable in that its optical system is simple in structure and its drive mechanism is also simple since there is no need to vary the distance between the sample and the light-source section in multiple steps.

In that case, the cell observation device according to the present invention may preferably be configured as follows:

the light-source section is capable of setting the wavelength of the output light at a plurality of values;

the measurement controller is configured to control the light-source section, the detector section and the moving section so as to sequentially switch the wavelength of the output light of the light-source section to a plurality of values at each measurement position and acquire a hologram for each wavelength;

the reconstructed image creator is configured to compute the phase information using the hologram data related to a plurality of different wavelengths acquired for the same measurement position; and the measurement monitoring image creator is configured to create a hologram image showing the light-intensity distribution within a portion or the entirety of the observation target area based on the hologram data related to one wavelength at each measurement position.

According to this configuration, when the wavelength of the output of the light-source section is sequentially switched to a plurality of values, the hologram data related to any one of the plurality of wavelengths may be used as the basis for creating the hologram image. For the earliest possible visualization of the hologram image at a measurement position at which the measurement has been completed, the measurement monitoring image creator should preferably create the hologram image based on the hologram data related to the wavelength which is used first for the measurement among the plurality of different wavelengths.

On the other hand, when a problem with the wavelength-switching operation of the output light in the light-source section needs to be recognized from the hologram image, it is preferable to create the hologram image based on the hologram data related to a wavelength which is used after the switching of the wavelength is performed at least a single time, instead of creating the hologram image based on the wavelength which is first used for the measurement among the plurality of different wavelengths. It is not always necessary to use hologram data related to the same wavelength at all measurement positions as the basis for creating the entire hologram image; i.e. it is possible to use hologram data related to different wavelengths and change the wavelength from one measurement position to another in creating the entire hologram image.

In a preferable mode of the cell observation device according to the present invention, the display processor is configured to display, on the display section, a screen on which the hologram image of a portion or the entirety of the observation target area created by the measurement monitoring image creator, and an operation element for allowing a user to issue a command to stop an ongoing measurement, are arranged.

In this mode of the cell observation device, the measurement controller may be configured to discontinue the ongoing measurement upon acknowledging an operation performed on the operation element. One example of the operation element is a button which is a type of graphical user interface (GUI) component.

According to this configuration, the user (measurement operator) watching the hologram image which is displayed almost in real time on the display section during the execution of the measurement can determine, for example, whether or not a foreign object which is not a cell is present, or whether or not the measurement is being properly performed. If the user has determined that the measurement should be discontinued, the user can immediately operate the operation element to command the device to discontinue the measurement. Thus, the measurement can be promptly discontinued with a simple operation.

As one mode of the present invention, the cell observation device may further include a range specifier for allowing a user to specify a range of the hologram image to be displayed on the display section, and the measurement monitoring image creator may be configured to create a hologram image related to the range specified by using the range specifier.

In normal situations, acquisition of the hologram data related to a measurement position is performed with the highest possible resolution. When a hologram image showing a specific range (e.g. the entire observation target area) is created for display, the resolution of the image needs to be lowered according to the size of the image, number of pixels of the screen of the display section and other relevant factors. The process of lowering the resolution must be performed for each measurement position. Accordingly, the processing load will be significantly reduced by decreasing the size of the range of the hologram image to be displayed on the display section, i.e. by decreasing the number of measurement positions included in that range. According to the previously described configuration, the user can limit the checking range by using the range specifier. This eliminates unnecessary processing to be performed by the measurement monitoring image creator, and thereby reduces the computation load.

In the present case, the measurement monitoring image creator may be configured to create the hologram image with an observing magnification corresponding to the range specified by using the range specifier.

This allows the user to easily recognize the presence of a small foreign object or similar object, and make a better judgment on whether or not the measurement should be discontinued.

In the cell observation device according to the present invention, the reconstructed image creator and the measurement monitoring image creator may be configured to have their respective functions implemented on the same computer or on the hardware circuits contained in the same housing. It is also possible to implement their respective functions on separate computers or completely separated hardware circuits. As a specific example, the functions of the reconstructed image creator, which must perform complex computations, may be implemented on a server computer (high-performance computer) connected via a communication network with a personal computer used for controlling the main unit of the digital holographic microscope which performs the measurement, while the functions of the measurement monitoring image creator may be implemented on that personal computer.

Advantageous Effects of Invention

By using the cell observation device according to the present invention, the user (measurement operator) can watch the hologram image displayed almost in real time during the execution of the measurement to check for an occurrence of a problem with the sample or improper handling in the measurement, without waiting for a phase image or intensity image to be displayed after the completion of complex computations based on hologram data acquired by the measurement. If such a problem has occurred, the user can promptly discontinue the measurement and avoid wasting time for the measurement. Consequently, the task of cell observation can be efficiently performed.

DESCRIPTION OF EMBODIMENTS

One embodiment of the cell observation device according to the present invention is hereinafter described with reference to the attached drawings.

Figure 1:
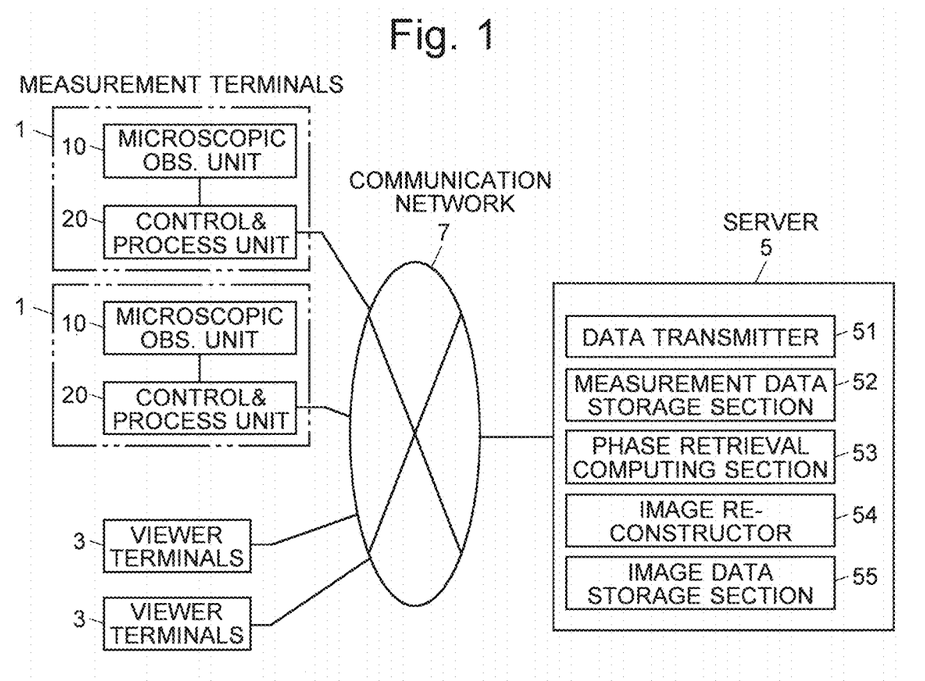
FIG. 1 is an overall configuration diagram of a cell observation device according to one embodiment of the present invention.
Figure 2:
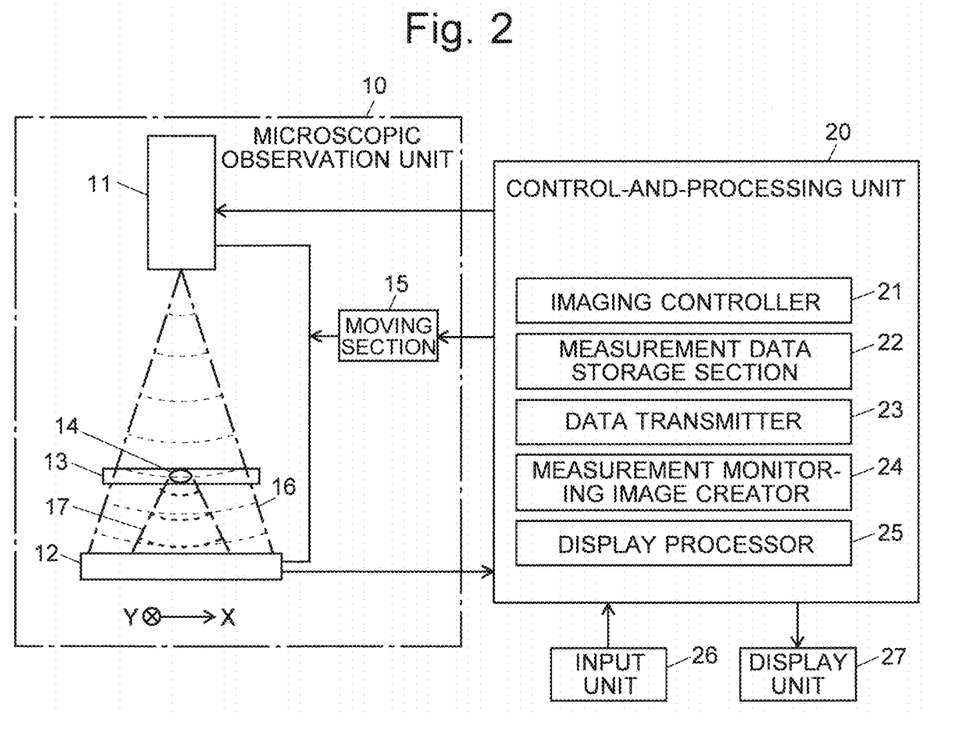
FIG. 2 is a schematic configuration diagram of a measurement terminal in the cell observation device according to the present embodiment.

FIG. 1 is an overall configuration diagram of the cell observation device according to the present embodiment. FIG. 2 is a schematic configuration diagram of a measurement terminal in the cell observation device according to the present embodiment.

The cell observation device according to the present embodiment includes measurement terminals 1, viewer terminals 3 and a server 5, which are connected to each other via a communication network 7, such as the Internet or intranet. FIG. 1 shows two measurement terminals 1 and two viewer terminals 3. Each of the two types of terminals may be provided in any appropriate number.

The server 5 is a high-performance computer and has functional blocks realized by dedicated software installed on the same computer, including a data transmitter 51, measurement data storage section 52, phase retrieval computing section 53, image reconstructor 54, and image data storage section 55.

The measurement terminal 1 includes a microscopic observation unit 10 and a control-and-processing unit 20. The microscopic observation unit 10 in the cell observation device according to the present embodiment is an in-line digital holographic microscope. As shown in FIG. 2, this microscope has a light-source section 11 including a laser diode and other components, as well as an image sensor 12. A cell culture plate 13 containing the cells 14 to be observed is placed between the light-source section 11 and the image sensor 12. The light-source section 11 and the image sensor 12 can be moved as an integral structure in the two directions of X and Y axes which are orthogonal to each other by a moving section 14 which includes a motor or similar drive source.

In order to prevent the drawing from being complex, FIG. 2 shows only one light-source section 11 and one image sensor 12, i.e. one set of light-source section and image sensor. There are actually four sets of light-source sections 11 and image sensors 12 which respectively face each other across the cell culture plate 13. As will be described later, the use of the four sets of light-source sections 11 and image sensors 12 enables the acquisition of holograms related to different measurement positions on the cell culture plate 13.

The control-and-processing unit 20 is actually a personal computer (PC) for controlling the operation of the microscopic observation unit 10 as well as processing data obtained with the microscopic observation unit 10. The same unit 20 has functional blocks realized by dedicated software installed on the PC, including an imaging controller 21, measurement data storage section 22, data transmitter 23, measurement monitoring image creator 24 and display processor 25. An input unit 26 which includes a keyboard and a pointing device (e.g. mouse), as well as a display unit 27, are connected to the control-and-processing unit 20.

As with the control-and-processing unit 20 in the measurement terminal 1, the viewer terminal 3 is actually a commonly used personal computer. A piece of dedicated software installed on this computer enables the viewer terminal 3 to receive data from the server 5 and display an appropriate type of image (such as a phase image or intensity image, which will be described later) created from those data.

An operation for acquiring hologram data in the cell observation device according to the present embodiment is hereinafter described with reference to FIGS. 3A-5.

Figure 4:
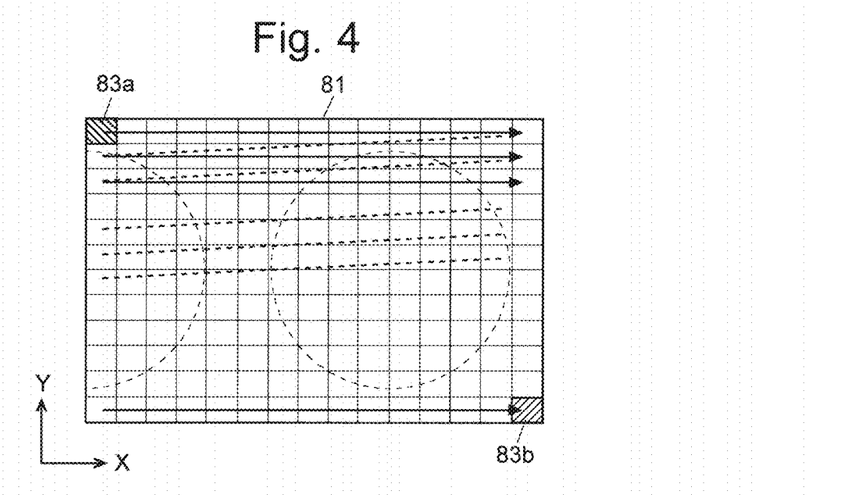
FIG. 4 is a diagram illustrating the process of sequentially changing the measurement position during a measurement in the cell observation device according to the present embodiment.
Figure 5:
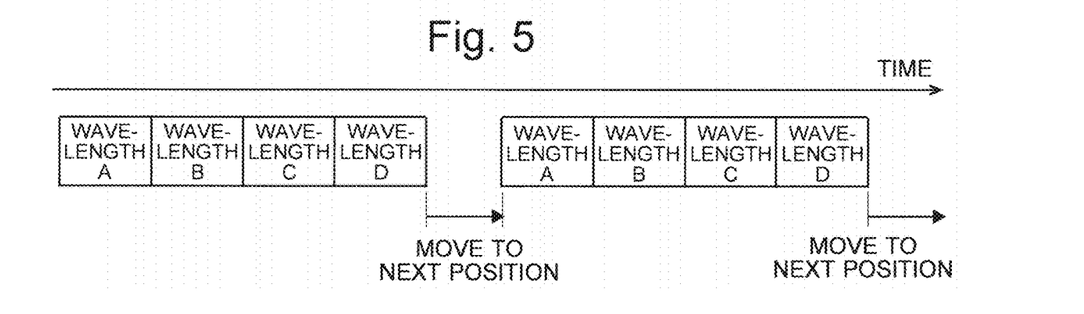
FIG. 5 is a diagram illustrating the timing of switching the wavelength during a measurement in the cell observation device according to the present embodiment.

FIGS. 3A-3D are conceptual diagrams for explaining an image-reconstructing process in the cell observation device according to the present embodiment. FIG. 4 is a diagram illustrating the process of sequentially changing the measurement position during a measurement in the cell observation device according to the present embodiment. FIG. 5 is a diagram illustrating the timing of switching the wavelength of the output light during a measurement in the cell observation device according to the present embodiment.

Figures 3A, 3B, 3C, 3D:
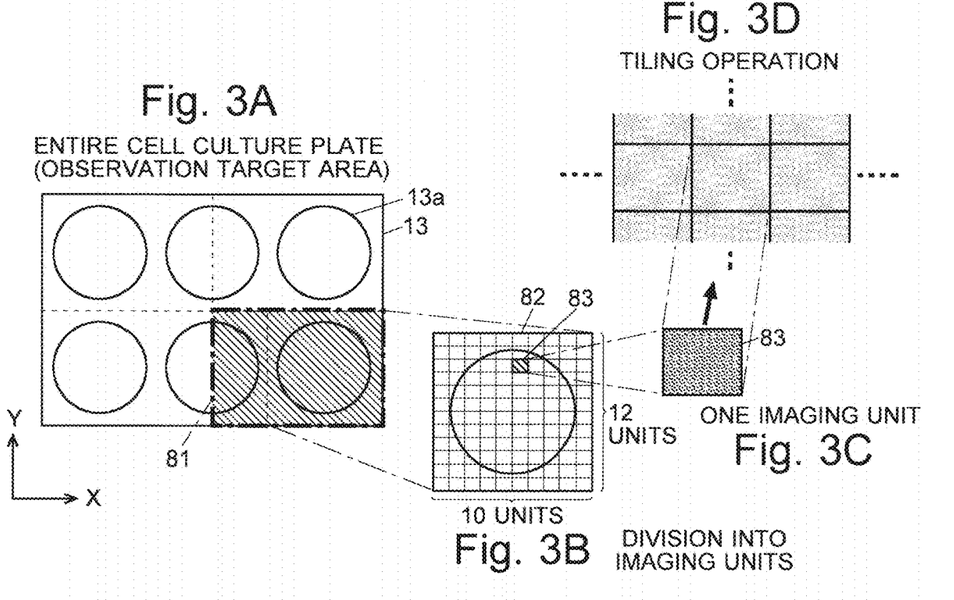
FIGS. 3A-3D are conceptual diagrams for explaining an image-reconstructing process in the cell observation device according to the present embodiment.

FIG. 3A is a schematic top view of the cell culture plate 13 used in the cell observation device according to the present embodiment. The cell culture plate 13 has six wells 13a each of which has a circular shape as viewed from above. The cells are cultured in all wells 13a. In the present case, the observation target area is the entire cell culture plate 13, i.e. the entire rectangular range including the six wells 13a. As noted earlier, the microscopic observation unit 10 has four sets of light-source sections 11 and image sensors 12. The four sets of light-source sections 11 and image sensors 12 are respectively responsible for the collection of hologram data of the four quarter ranges 81 formed by equally dividing the entire area of the cell culture plate 13 into four sections. In other words, the task of collecting hologram data covering the entire cell culture plate 13 is shared by the four sets of light-source sections 11 and image sensors 12.

The range whose image can be taken at one time with one set of light-source section 11 and image sensor 12 is a range corresponding to one of the imaging units 83 shown in FIGS. 3B and 3C which are formed by dividing a substantially square range 82 including a single well 13a within one quarter range 81 into 10 units in the X direction and 12 units in the Y direction. One quarter range 81 consists of 15×12=180 imaging units 83. Each of those imaging units 83 corresponds to a "measurement position" in the present invention. The four light-source sections 11 and four image sensors 12 are respectively arranged in two planes which are both parallel to the X-Y plane, with each plane including the four light-sources 11 or the four image sensors 12 located at or around the four corners of a rectangle of the same size as the quarter range 81. Those light-source sections and image sensors are operated to simultaneously acquire holograms related to four different imaging units 83 on the cell culture plate 13.

For the collection of data for the cell culture plate 13, an observer initially sets the cell culture plate 13 at a predetermined position in the microscopic observation unit 10, with the cells (pluripotent cells) 14 cultured on the plate 13 as the object to be observed. After entering necessary information from the input unit 26, such as the identification number which identifies the cell culture plate 13 as well as the date and time of the measurement, the observer issues a command to execute the measurement. Upon receiving the measurement execution command, the imaging controller 21 controls each relevant section of the microscopic observation unit 10 and initiates the measurement.

That is to say, under the control of the imaging controller 21, each light-source section 11 illuminates a predetermined area (one imaging unit 83) on the cell culture plate 13 with a beam of coherent light having a small spread angle of approximately 10 degrees. The coherent light which has passed through the cell culture plate 13 and the cells 14 (object beam 17) reaches the image-sensor section 12, interfering with the light which has passed through the areas near the cells 14 on the cell culture plate 13 (reference beam 16). The object beam 17 is a beam of light which has undergone a change in phase when passing through the cells 14, whereas the reference beam 16 is a beam of light which does not undergo such a change in phase due to the cells 14 since this light does not pass through the cells 14. Accordingly, on the detection surface (imaging plane) of each image sensor 12, an interference image (i.e. hologram) of the object beam 17 which has undergone the change in phase due to the cells 14 and the reference beam 16 with no such change in phase form is formed. The image sensor 12 produces hologram data, i.e. the two-dimensional light-intensity distribution data corresponding to the hologram.

As described earlier, coherent beams are almost simultaneously cast from the four light-source sections 11 onto the cell culture plate 13, and hologram data for areas corresponding different imaging units 83 on the cell culture plate 13 are acquired with the four image sensors 12. After the completion of the measurement at one measurement position, the light-source sections 11 and the image sensors 12 are moved by the moving section 15 in their respective X-Y planes in a stepwise manner by a distance corresponding to one imaging unit 83 in the X or Y direction. For example, as shown in FIG. 4, each set of light-source section 11 and image sensor 12 is moved to sequentially change their position with respect to the cell culture plate 13 so that the measurement position starts from the first imaging unit 83a within one quarter range 81 and sequentially moves in the X direction until it reaches the last imaging unit 83b at which the measurement is performed for the last time. In this manner, the measurement for the 180 imaging units 83 included in one quarter range 81 is carried out. The measurement for the entire cell culture plate 13 is achieved by the entire arrangement of the four sets of light-source sections 11 and image sensors 12.

In the cell observation device according to the present embodiment, holograms related to different multiple wavelengths of light (in the present example, four wavelengths) are acquired for each object, i.e. for each imaging unit 83, in order to perform computations for retrieving phase information on the server 5. To this end, the wavelength of the coherent light generated from the light-source section 11 is sequentially set at four predetermined values during the measurement for an area corresponding to one imaging unit 83 on the cell culture plate 13, and hologram data is acquired for each wavelength of light. Specifically, as shown in FIG. 5, the wavelength of the output light is sequentially set at A, B, C and D at one measurement position, and hologram data is acquired for each wavelength. After one sequence of data acquisition has been completed, the light-source section 11 and the image sensor 12 are moved to the next measurement position by the moving section 15.

In this manner, in the microscopic observation unit 10, four sets of hologram data related to the four wavelengths (A, B, C and D) are exhaustively acquired for the area corresponding to the 720 imaging units 83 on the cell culture plate 13.

The hologram data acquired with the four image sensors 12 in the microscopic observation unit 10 in the previously described manner are temporarily stored in the measurement data storage section 22 in the control-and-processing unit 20. The data transmitter 23 successively transfers hologram data stored in the measurement data storage section 22 to the server 5 via the communication network 7 along with the property information including the date and time of the measurement. The measurement terminals 1 can be simultaneously operated. The hologram data acquired with those measurement terminals 1 are gathered by the single server 5 via the communication network 7. The hologram data to be sent from each measurement terminal 1 to the server 5 may be "raw" or unprocessed data. It is also possible to preprocess the hologram data as needed for such purposes as the correction of the causes of errors specific to each measurement terminal 1 before transmitting the data to the server 5.

The data transmitter 51 in the server 5 receives hologram data from each measurement terminal 1 and accumulates those data in the measurement data storage section 52 along with the identification information for identifying the measurement terminal 1 and the property information entered at the time of the imaging, such as the identification information of the cell culture plate as well as the date and time of the measurement. While the data are being collected in this manner, or after the data have been collected, the phase retrieval computing section 53 reads appropriate hologram data from the measurement data storage section 52 and performs the light-wave propagation calculation to retrieve phase information as well as compute amplitude information. The spatial distributions of the phase information and amplitude information are obtained for each imaging unit 83. After the phase information and amplitude information have been completely obtained for all imaging units 83, the image reconstructor 54 creates a phase image and intensity image of the entire observation target area based on the phase information and amplitude information.

Specifically, the image reconstructor 54 creates a phase image for the observation target area, i.e. the entire cell culture plate 13, by reconstructing the phase image of each imaging unit 83 based on the two-dimensional distribution of the phase information computed for each imaging unit 83 and performing the tiling operation (see FIG. 3D) in which the reconstructed phase images each of which covers a small range are connected to each other. Needless to say, it is preferable to perform an appropriate correcting operation for seamless connection of the phase images at the boundaries of the imaging units 83 in the tiling operation. For such a calculation of the phase information as well as the reconstruction of the images, an appropriate algorithm disclosed in commonly known documents may be used, such as the ones disclosed in Patent Literature 1 or 2. Reconstructed images obtained by a normal processing method has the highest resolution which is in principle determined by the acquired hologram data. A plurality of phase images whose levels of resolution (magnification) are decreased in a stepwise manner by the binning or similar processing may additionally be created from the phase image having the highest resolution. The image data constituting the phase images created in this manner are stored in the image data storage section 55.

Figure 6:
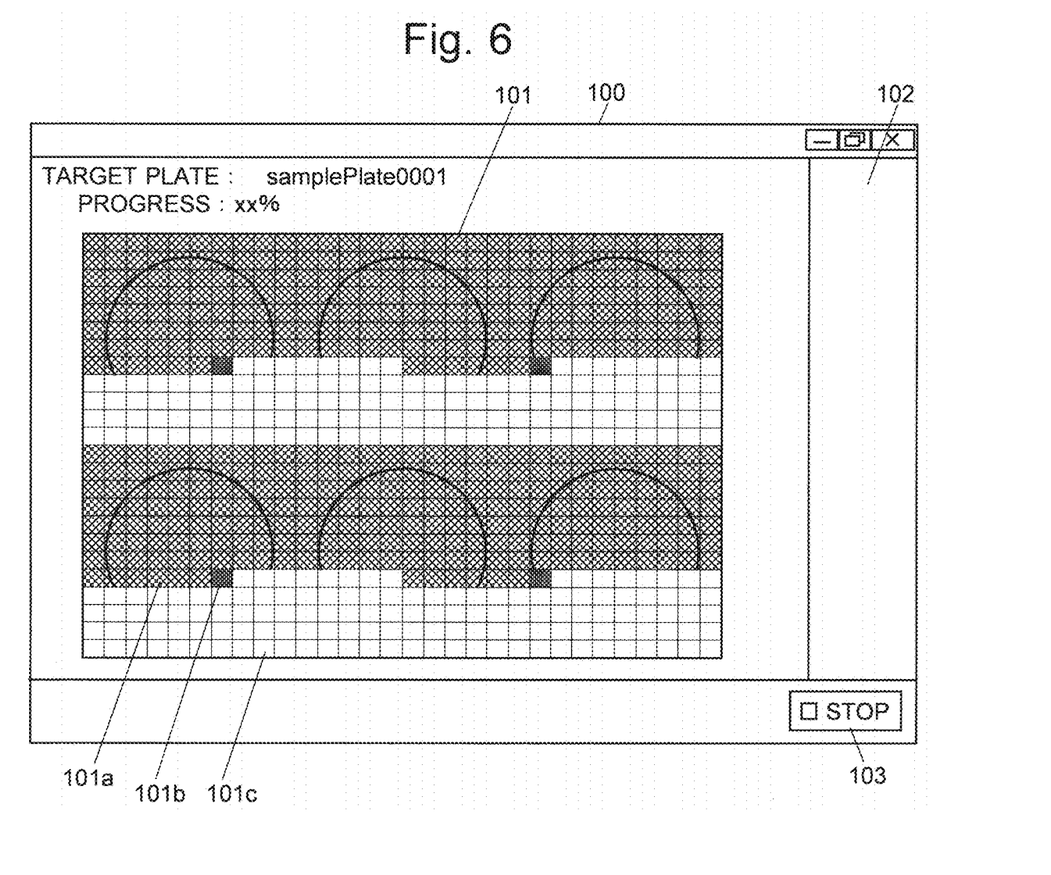
FIG. 6 is a model diagram showing one example of a real-time image display screen in the cell observation device according to the present embodiment.

Although this depends on the power of the server 5, the processes performed in the phase retrieval computing section 53 and image reconstructor 54 are complex and require a considerable amount of time. Therefore, it is impossible to view the phase image or intensity image based on the result of the measurement immediately after the completion of the entire measurement on the measurement terminal 1. Accordingly, for example, even if a foreign object is present in a well 13a, the measurement operator cannot recognize it on the phase image or intensity image until a considerably later point in time. In view of this, the cell observation device according to the present invention is configured to allow the operator to quickly recognize the presence of a foreign object or an occurrence of a problem with the measurement during the execution of the measurement as follows:

Before the execution of the measurement, the measurement operator performs a predetermined operation on the input unit 26. Then, the display processor 25 displays a real-time image display screen 100 as shown in FIG. 6 on the display unit 27. The real-time image display screen 100 includes an image display area 101 and information display area 102. Additionally, a "stop" button is located at the lower right corner of the screen. The information display area 102 shows the property information of the cell culture plate 13 which is under measurement (or is about to be subjected to the measurement), such as the name (plate name) and identification number (plate ID). It should be noted that the real-time image display screen 100 in FIG. 6 shows a situation in which the measurement is already being executed and a real image is displayed in the image display 101. No real image is displayed in the image display area 101 before the beginning of the measurement.

After the measurement has been initiated, hologram data at a plurality of wavelengths are acquired for each imaging unit 83 on the cell culture plate 13, and those data are stored in the measurement data storage section 22, as described earlier. In the middle of this operation, when hologram data related to the first wavelength (i.e. wavelength "A") for one imaging unit 83 has been acquired, the measurement monitoring image creator 24 concurrently creates a hologram image showing the two-dimensional distribution of the light intensity based on that hologram data. The size, or resolution, of the thus created hologram image depends on the range of the image to be displayed in the image display area 101. In the example shown in FIG. 6, a hologram image of the entire cell culture plate 13 is displayed in the image display area 101, in which case the hologram image corresponding to one imaging unit 83 has the smallest size. In other words, in this case, the measurement monitoring image creator 24 creates a thumbnail image showing the two-dimensional distribution of the light intensity within one imaging unit 83 with the lowest resolution, based on the hologram data acquired from the area corresponding to that imaging unit 83. The display processor pastes the thumbnail image of the created hologram image in a predetermined area within the image display area 101 of the real-time image display screen 100.

Thus, the measurement monitoring image creator 24 creates the thumbnail image which is a size-reduced version of the hologram image obtained without performing any substantial image processing other than lowering the resolution of the two-dimensional distribution of the light intensity acquired by the measurement. The display processor 25 displays that image with no change. Accordingly, as soon as the hologram data at a specific wavelength has been acquired, the hologram image based on that data is almost instantaneously displayed on the display unit 27 (i.e. in almost real time). Subsequently, new hologram data related to wavelength "A" for an area corresponding to the next imaging unit 83 is acquired, and a thumbnail image is created by reducing the hologram image based on that data. Then, the new thumbnail image is added to the display on the screen of the display unit 27. In FIG. 6, the thumbnail images already displayed in this manner are denoted by reference sign 101a. Thumbnail images which are currently under measurement or being created are denoted by reference sign 101b. Thumbnail images which remain to be subjected to the measurement are denoted by reference sign 101c.

Figure 8:
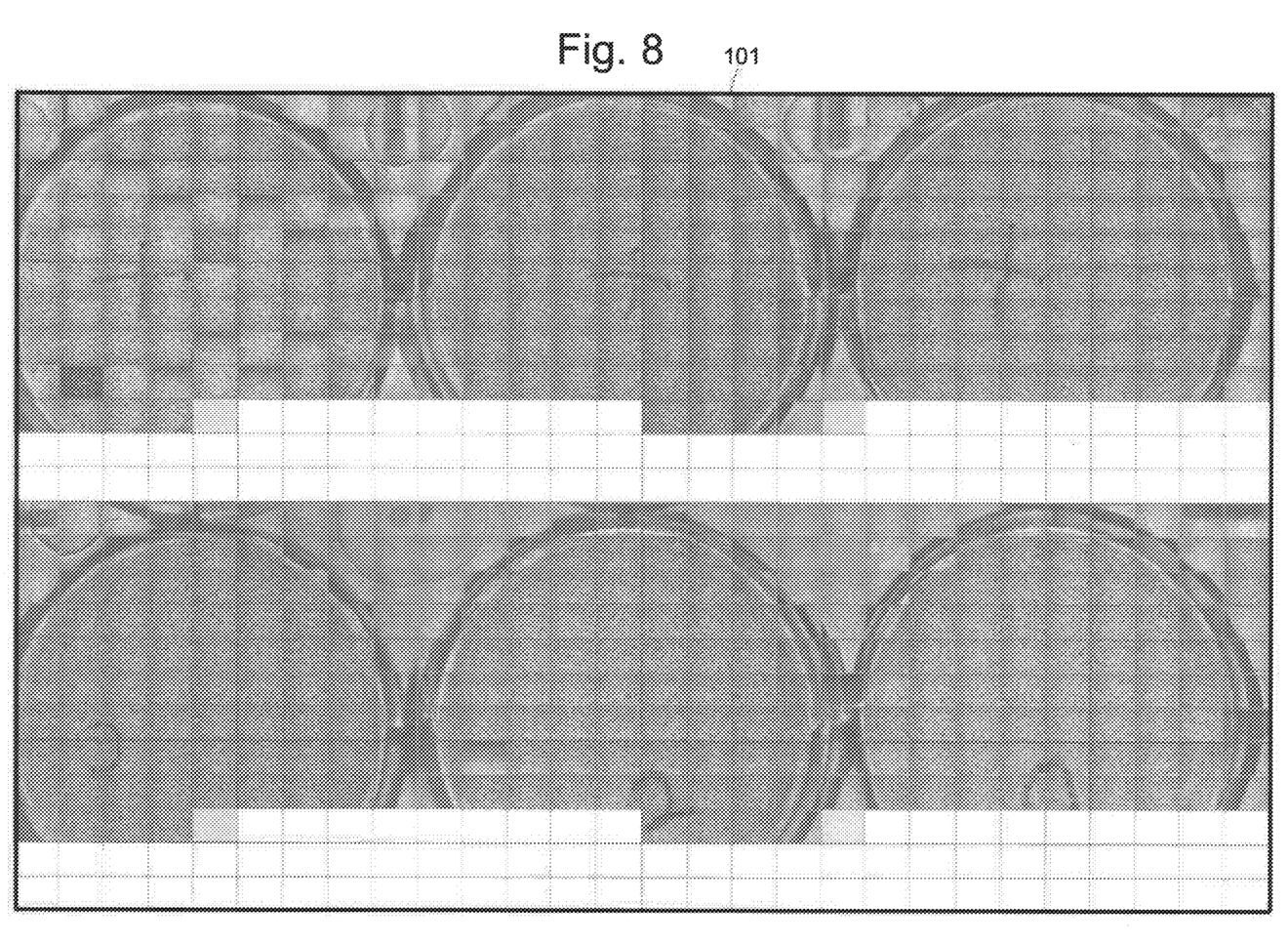
FIG. 8 shows an actual example of a display image to be displayed in the real-time image display screen in the cell observation device according to the present embodiment

FIG. 8 shows an actual example of the display screen shown in the real-time image display screen 100. As can be seen, although the hologram image displayed in the image display area 101 is simple hologram data, the image provides a clear view of such structures as the step part at the edge of the wells 13a as well as foreign objects that are sufficiently larger in height than the cells and are not transparent. The same image also shows many phenomena associated with problems with the device, such as a light-sour section 11 not generating output light or an image sensor 12 having a damaged pixel, as well as improper handling in the measurement. Accordingly, during the execution of the measurement, the measurement operator watches the hologram image displayed in the image display area 101 and clicks the "stop" button 103 using the input unit 26 when it is possible to conclude that there is a certain problem. Upon acknowledging the clicking operation, the imaging controller 21 promptly discontinues the measurement. Thus, when there is a problem with the measurement, the operator can promptly discontinue the measurement and avoid wasting time for the remaining measurement. Furthermore, for example, when a foreign object is possibly present, the operator can promptly examine the cell culture plate 13 to identify its cause or once again perform the same measurement.

Figure 7:
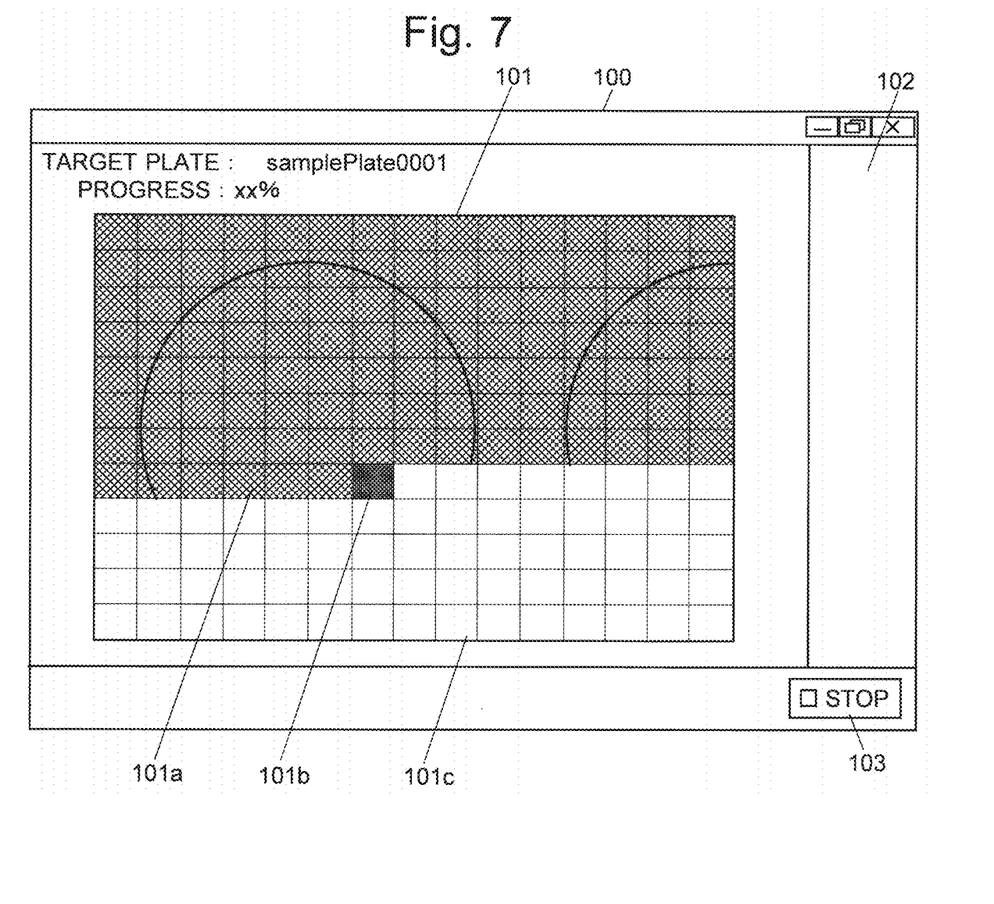
FIG. 7 is a model diagram showing another display example of the real-time image display screen in the cell observation device according to the present embodiment.

In the example shown in FIG. 6, the hologram image of the entire cell culture plate 13 is displayed in the image display area 101. It is also possible to selectively display a portion of the image in the image display area 101. FIG. 7 shows an example in which a hologram image corresponding to one quarter range 81 is displayed in the image display area 101. By displaying such an enlarged image that shows only an area which the measurement operator wants to check, it becomes easier, for example, to locate a small foreign object. The enlargement also reduces the number of areas corresponding to the imaging units 83 to be displayed on the image display area 101. This means that there are fewer target areas to be subjected to the image processing for lowering the resolution when the thumbnail image with the lowered resolution is created based on the hologram data in the previously described manner. This reduces the load on the CPU of the computer and contributes to an acceleration of the image display or other processing.

The microscopic observation unit 10 in the previous embodiment is an in-line digital holographic microscope. The type of microscopic observation unit 10 is not limited to the in-line type; it may be any type of device which can acquire a hologram for each measurement position within art observation target area. Accordingly, an off-axis or phase-shift digital holographic microscope may also be used. The present invention is not limited to a device which acquires a plurality of holograms by sequentially switching the wavelength of the output light of the light-source section 11. For example, the present invention may be applied in a device which acquires a plurality of holograms by changing the position of the cell culture plate in multiple steps in the Z direction which is orthogonal to both X and Y axes.

In the previous embodiment, the phase retrieval and other computational operations are performed on the server 5 which is connected with the measurement terminals 1 via the communication network 7. It is naturally possible to configure the device as a standalone system which performs all operations.

Furthermore, it should be understood that the previously described embodiment and its variations are mere examples of the present invention, and any change, modification or addition appropriately made within the spirit of the present invention will naturally fall within the scope of claims of the present application.

REFERENCE SIGNS LIST

1 . . . Measurement Terminal
10 . . . Microscopic Observation Unit
11 . . . Light-Source Section
12 . . . Image Sensor
13 . . . Cell Culture Plate
13a . . . Well
14 . . . Cell
15 . . . Moving Section
16 . . . Reference Beam
17 . . . Object Beam
20 . . . Control-and-Processing Unit
21 . . . Imaging Controller
22 . . . Measurement Data Storage Section
23 . . . Data Transmitter
24 . . . Measurement Monitoring Image Creator
25 . . . Display Processor
26 . . . Input Unit
27 . . . Display Unit
3 . . . Viewer Terminal
5 . . . Server
51 . . . Data Transmitter
52 . . . Measurement Data Storage Section
53 . . . Phase Retrieval Computing Section
54 . . . Image Reconstructor
55 . . . Image Data Storage Section
7 . . . Communication Network
100 . . . Real-Time Image Display Screen
101 . . . Image Display Area
102 . . . Information Display Area
103 . . . "Stop" Button

The invention claimed is:

1. A cell observation device employing a holographic microscope, comprising:
   a) a light-source section configured to generate coherent output light;
   b) a detector section configured to obtain a hologram which is an interference pattern formed by reference wave and object wave when a sample containing a cell is illuminated with the output light of the light-source section;
   c) a moving section configured to move either the light-source section and the detector section or the sample, or both, so as to change a measurement position on the sample;
   d) a measurement controller configured to control the light-source section, the detector section and the moving section so as to repeatedly change the measurement position from one position to another on the sample by the moving section and acquire a hologram at each measurement position within a predetermined observation target area;
   e) a reconstructed image creator configured to compute phase information based on hologram data acquired with the detector section under a control of the measurement controller, and to create an image showing a two-dimensional distribution of the phase information;
   f) a measurement monitoring image creator configured to create, in real time, a hologram image related to a range specified by using the below mentioned range specifier, based on the hologram data acquired with the detector section on measurement positions for which the measurement is already completed;
   g) a range specifier configured to allow a user to specify, within the hologram image, a range to be displayed on a display section; and
   h) a display processor configured to display, on the display section, the hologram image created in real time by the measurement monitoring image creator during the execution of the measurement under the control of the measurement controller.

2. The cell observation device according to claim 1, wherein:
   the light-source section is capable of setting a wavelength of the output light at a plurality of values;
   the measurement controller is configured to control the light-source section, the detector section and the moving section so as to sequentially switch the wavelength of the output light of the light-source section to a plurality of values at each measurement position and acquire a hologram for each wavelength;
   the reconstructed image creator is configured to compute the phase information using the hologram data related to a plurality of different wavelengths acquired for the same measurement position; and
   the measurement monitoring image creator is configured to create a hologram image based on the hologram data related to one wavelength at each measurement position.

3. The cell observation device according to claim 2, wherein:
   the measurement monitoring image creator is configured to create the hologram image based on the hologram data related to the wavelength which is used first for the measurement among the plurality of different wavelengths.

4. The cell observation device according to claim 1, wherein:
   the display processor is configured to display, on the display section, a screen on which the hologram image created by the measurement monitoring image creator, and an operation element for allowing a user to issue a command to stop an ongoing measurement, are arranged.

5. The cell observation device according to claim 4, wherein:
   the measurement controller is configured to discontinue the ongoing measurement upon acknowledging an operation performed on the operation element.

6. The cell observation device according to claim 5, wherein:
   the measurement monitoring image creator is configured to create the hologram image with an observing magnification corresponding to the range specified by using the range specifier.

* * * * *